United States Patent [19]

Giovanniello

[11] Patent Number: 5,358,694

[45] Date of Patent: * Oct. 25, 1994

[54] METHOD FOR PREPARING BASIC ALUMINUM HALIDES AND PRODUCT PRODUCED THEREFROM

[75] Inventor: Rocco Giovanniello, Port Jervis, N.Y.

[73] Assignee: Westwood Chemical Corporation, Middletown, N.Y.

[*] Notice: The portion of the term of this patent subsequent to Oct. 3, 2006 has been disclaimed.

[21] Appl. No.: 409,654

[22] Filed: Sep. 19, 1989

Related U.S. Application Data

[63] Continuation-in-part of Ser. No. 81,638, Aug. 3, 1987, Pat. No. 4,871,525, which is a continuation-in-part of Ser. No. 922,753, Oct. 24, 1986, abandoned, which is a continuation of Ser. No. 817,047, Jan. 8, 1986, abandoned.

[51] Int. Cl.$^5$ .................... A61K 7/38; C01F 7/56
[52] U.S. Cl. ........................ 423/462; 424/68
[58] Field of Search .................... 423/462; 424/68

[56] References Cited

U.S. PATENT DOCUMENTS

| | | | |
|---|---|---|---|
| 2,196,016 | 4/1990 | Huehn et al. | 423/462 |
| 3,476,509 | 11/1969 | Jones | 423/462 |
| 3,507,896 | 4/1970 | Jones et al. | 423/462 |
| 3,891,745 | 6/1975 | Bellan et al. | 423/462 |
| 3,904,741 | 9/1975 | Jones et al. | 423/462 |
| 3,953,584 | 4/1976 | Danner et al. | 423/462 |
| 4,038,373 | 7/1977 | Merkel | 423/462 |
| 4,053,570 | 10/1977 | Merkl | 423/462 |
| 4,359,456 | 11/1982 | Gosling et al. | 423/462 |
| 4,859,446 | 8/1989 | Abrutyn et al. | 423/462 |
| 4,871,525 | 10/1989 | Giovanniello et al. | 423/462 |
| 4,944,933 | 7/1990 | Inward | 423/462 |

FOREIGN PATENT DOCUMENTS

| | | | |
|---|---|---|---|
| 191628 | 8/1986 | . | |
| 2048229 | 12/1980 | United Kingdom | 423/462 |

OTHER PUBLICATIONS

Reach ®Reheis Enhanced Efficacy Aluminum Chlorhydrates.

*Primary Examiner*—Jeffrey E. Russel
*Attorney, Agent, or Firm*—Anthony Lagani, Jr.

[57] ABSTRACT

Polymeric basic aluminum halides having the empirical formula:

$$Al_2(OH)_{6-y}X_y$$

where X is chlorine, bromine or iodine, y has a numerical value from 0.7 to 3, and whose polymer distribution as characterized by size exclusion chromatography is:
(a) 100% of the polymers are found in Bands II, III and IV, and
(b) Band III contains at least 25% of the polymer; are obtained by reacting aluminum metal with HX in water at a temperature of about 70° C. to about 100° C., where X is halogen, wherein the concentration of product in solution is about 8 to about 35 wt. %.

42 Claims, 8 Drawing Sheets

Aluminum Chlorhydrate Stage
At 1.94:1 Al/Cl Atomic Ratio

CONVENTIONAL 50% ACH

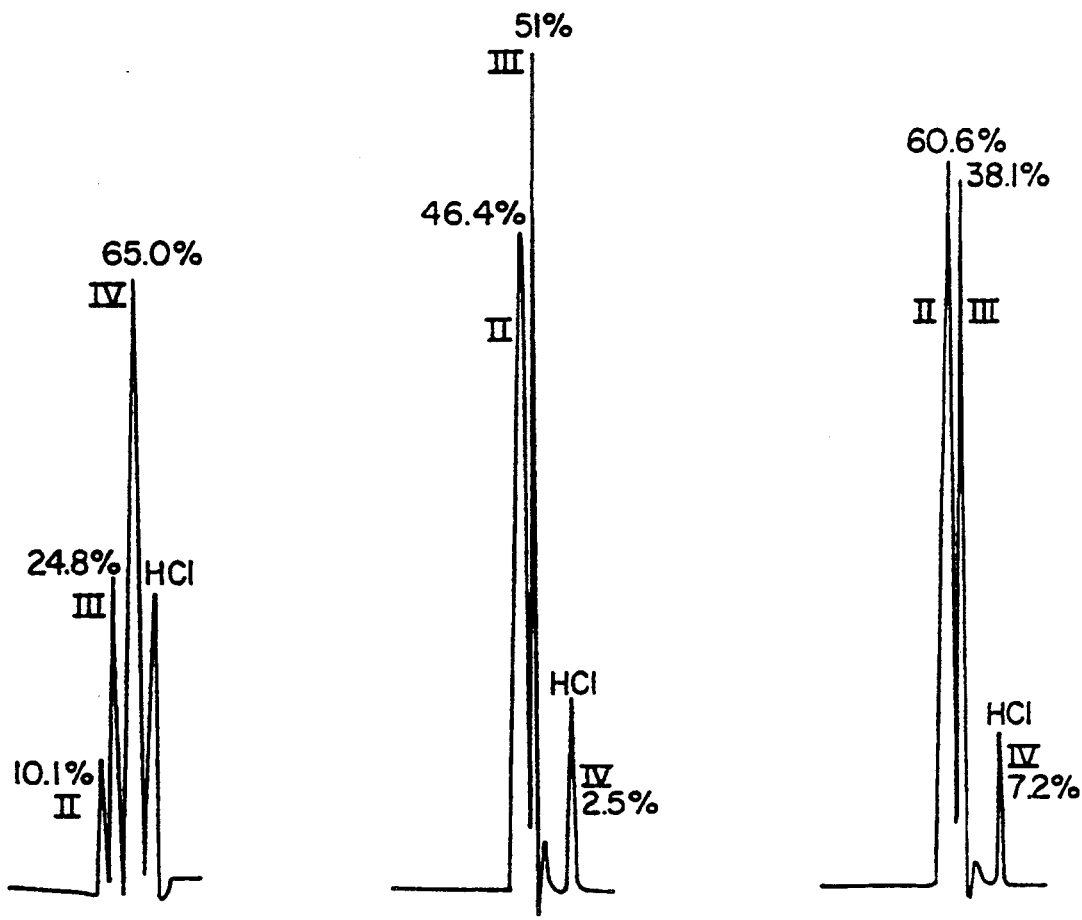

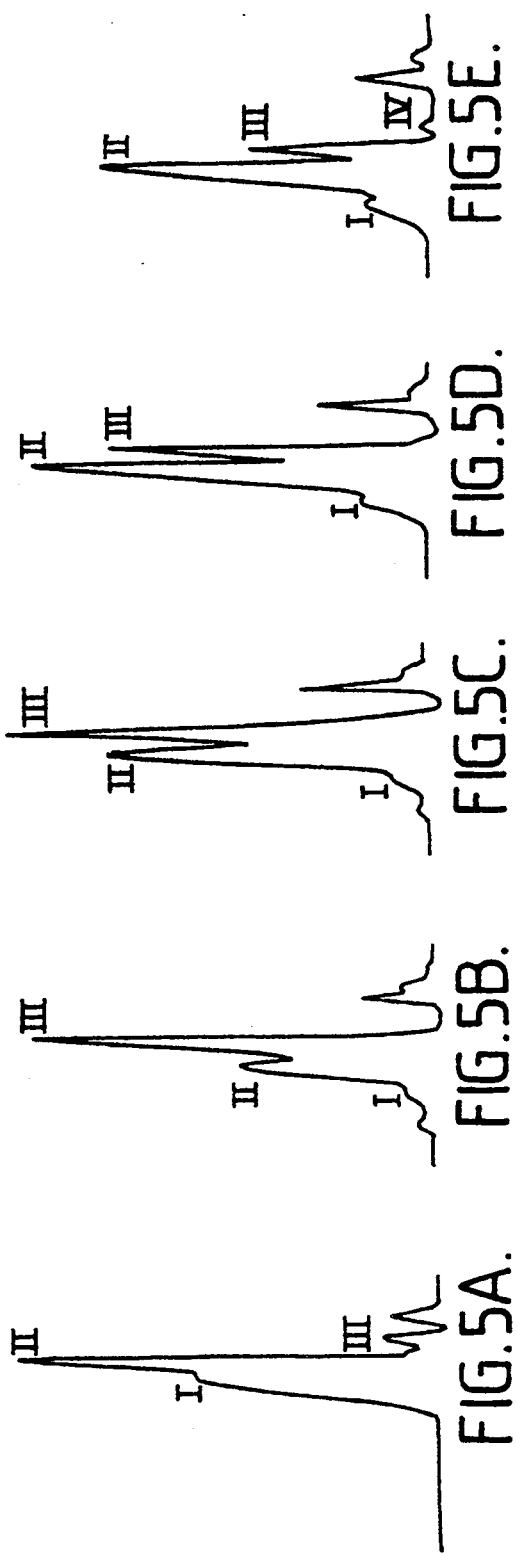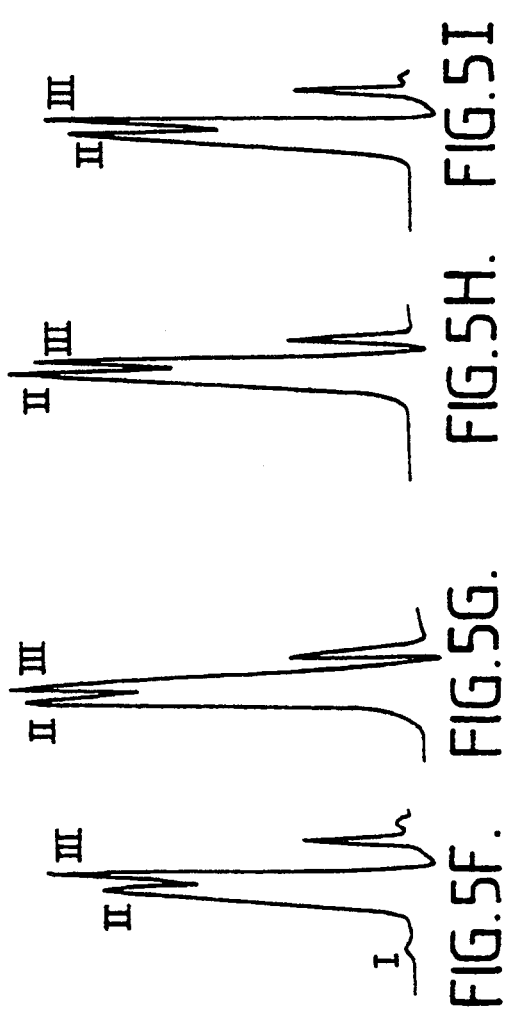

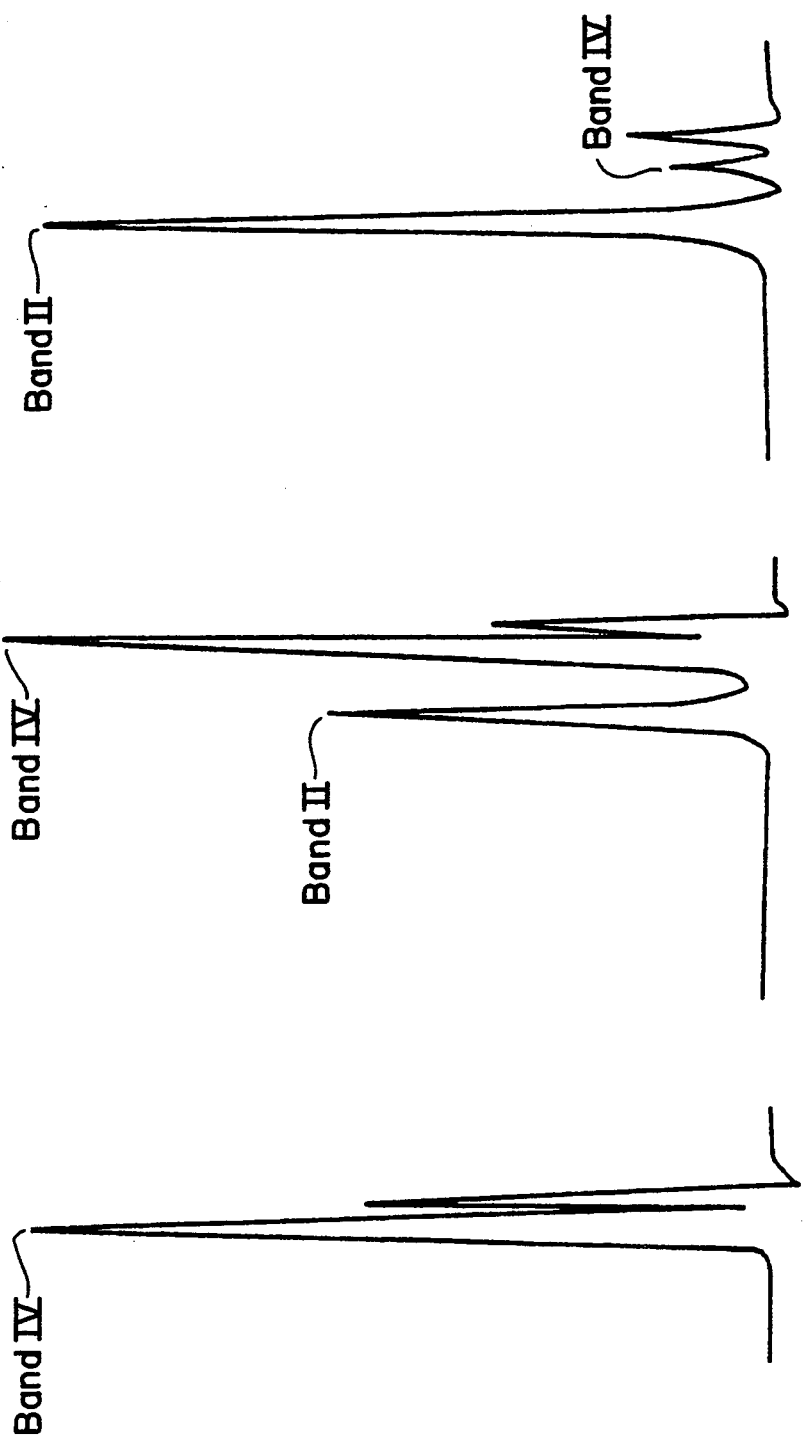

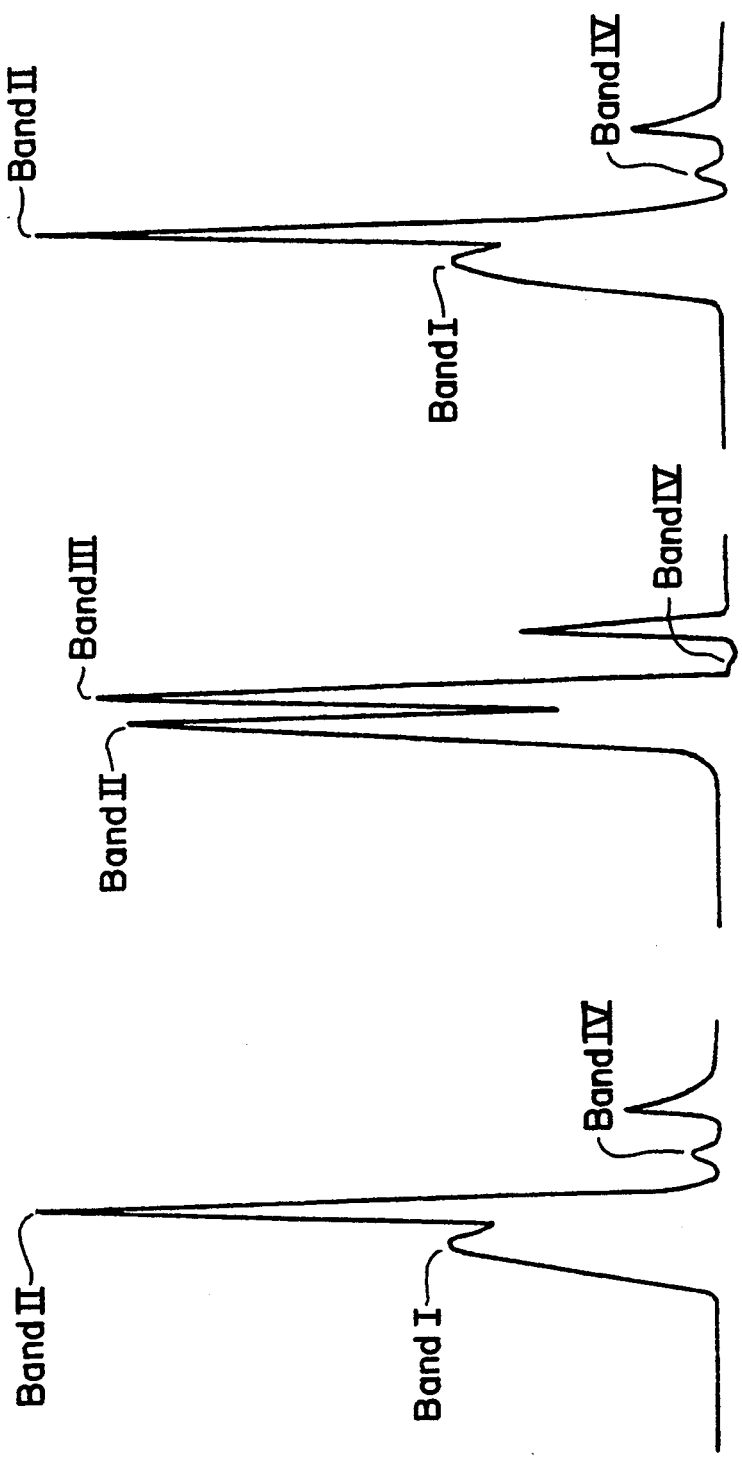

METHOD FOR PREPARING BASIC ALUMINUM HALIDES AND PRODUCT PRODUCED THEREFROM

CROSS-REFERENCE TO RELATED APPLICATIONS

This application is a continuation-in-part of U.S. patent application Ser. No. 081,638, filed Aug. 3, 1987, now U.S. Pat. No. 4,871,525, which is in turn a continuation-in-part of U.S. application Ser. No. 922,753, filed Oct. 24, 1986, now abandoned, which is itself in turn a continuation of U.S. patent application Ser. No. 817,047, filed Jan. 8, 1986, now abandoned.

FIELD OF THE INVENTION

This invention relates to basic aluminum halides. In particular, it relates to a process for preparing basic aluminum halide compositions having high antiperspirant activity and to the compositions prepared by the method of this invention.

BACKGROUND OF THE INVENTION

Basic aluminum halides (also referred to as aluminum halohydrates) have long been known to possess antiperspirant activity. These antiperspirant compositions are available in the form of polymeric compositions having the empirical formula:

$$Al_2(OH)_{6-y}X_y$$

wherein X is chlorine, bromine or iodine and y has a numerical value from about 0.7 to about 3. However, it is only in recent studies, as described in U.S. Pat. No. 4,359,456 (the '456 patent), that it has been shown by size exclusion chromatography that basic aluminum halides are composed of individual polymer bands which pertain to different molecular weight groups of the compound. In these studies of basic aluminum halides obtained by conventional methods of preparation it was shown that it can further be broken down from high molecular weight polymers into larger amounts of lower molecular weight polymers by diluting concentrated aqueous solutions thereof to lower aqueous concentrations and treating with heat and or aging at room temperature to produce more effective antiperspirants as shown in sweat reduction panel studies.

The '456 patent describes processes for the preparation of improved antiperspirant compositions of aluminum halohydrates, which involve heating a 2.5 to 8.5% by weight, based on aluminum, of an aqueous solution of an aluminum halohydrate of the formula:

$$Al_2(OH)_{6-y}X_y$$

where X and y are as defined above, at a temperature of 50° to 140° C. for a period of time to impart to the aluminum product certain desired properties in respect of size exclusion chromatogram test bands. The products thus obtained from these processes have good antiperspirant activity, but the processes do not provide compositions containing larger amounts of the lower molecular weight polymers with a narrow polydispersity which are believed to possess greater antiperspirant activity.

In addition to the '456 patent, processes for the preparation of antiperspirant basic aluminum halides are shown in U.S. Pat. Nos. 3,507,896; 3,891,745; 3,904,741; 4,038,373 and 4,053,570. However, none of these patents disclose polymeric compositions possessing the desired amounts of the lower molecular weight polymers as measured by the size exclusion chromatogram test band.

SUMMARY OF THE INVENTION

It has surprisingly been found that polymeric basic aluminum halides having the empirical formula:

$$Al_2(OH)_{6-y}X_y \cdot nH_2O$$

wherein y has a numerical value from about 0.7 to about 3, X is chlorine, bromine or iodine; n is a numeral from about 0.8 to about 4.0 and the polymer distribution as characterized by size exclusion chromatogram test is: (a) 100% of the aluminum containing polymers are found in bands II, III and IV, and (b) band III contains at least 25% of the polymers, can be prepared by reacting an aluminum metal with a halogen compound having the formula HX were X is as previously defined, while maintaining the temperature of the reaction mixture at about 50° C. to about 100° C. The aluminum metal is preferably in the form of pellets or powder.

The amount of water used is such as to have the final concentration of the polymer solution, in percent by weight, in the range of about 8 to about 35%, preferably about 8 to about 25%, more preferably about 15 to about 25%, and most preferably from about 17 to about 22% by weight. The reaction temperatures are preferably in the range of about 95° to about 100° C.

BRIEF DESCRIPTION OF THE DRAWINGS

FIGS. 2 to 4 are chromatograms of products as they form during various states of the process of this invention.

FIG. 5A–I represents the chromatographs for comparative examples and is more completely described as follows:

FIG. 5A Standard 50% basic aluminum chloride solution used for tests 5B–5F.

FIG. 5B 10% solution of standard basic aluminum chloride heated for 6 hrs. at 95° C. and cooled to room temperature.

FIG. 5C 15% solution of standard basic aluminum chloride heated for 6 hrs. at 95° C. and cooled to room temperature.

FIG. 5D 20% solution of standard basic aluminum chloride heated for 6 hrs. at 95° C. and cooled to room temperature.

FIG. 5E 25% solution of standard basic aluminum chloride heated for 6 hrs. at 95° C. and cooled to room temperature.

FIG. 5F 20% solution of standard basic aluminum chloride heated for 72 hrs. at 95° C. and cooled to room temperature.

FIG. 5G 20% solution of basic aluminum chloride prepared by the process of this invention at 95° C., and sampled immediately for chromatogram testing.

FIG. 5H 20% solution of basic aluminum chloride prepared by the method of this invention at 95° C., maintained at 95° C. for 6 hours after completion of the reaction, sampled at 95° C. and tested.

FIG. 5I 20% solution of basic aluminum chloride prepared by the method of this invention at 95° C., maintained at 95° C. for 72 hours after completion of the reaction, sampled at 95° C. and tested.

FIGS. 8A–8C are chromatograms for aluminum chlorhydrates prepared using the method of U.S. Pat. No. 3,891,745.

FIGS. 9A–9C are chromatograms for conventional Aluminum Chlorhydrate and Activated Aluminum Chlorhydrate prepared by the process of this invention.

FIG. 10 is a plot of the Band I content as a function of time of the product of U.S. Pat. No. 4,359,456.

DETAILED DESCRIPTION OF THE INVENTION

Figure 1:
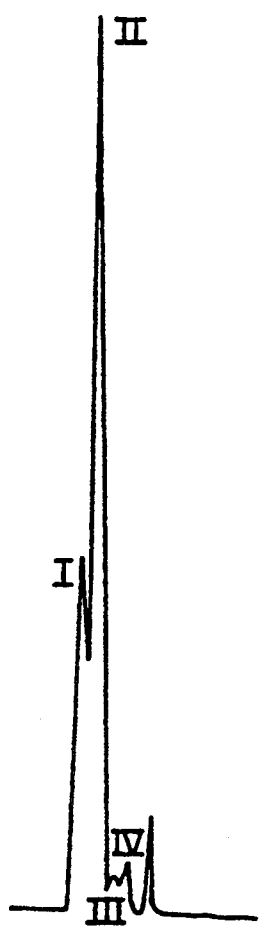
FIG. 1 is a chromatogram of a product made by a known conventional method as described in Example 1.

This invention relates to an improved method for preparing an aluminum chlorhydrate having improved antiperspirant activity as determined by the existence of a band III component of polymer of at least 25 wt. %. The product of this invention is substantially free of any Band I component. Additionally, this invention relates to a complex of the aforementioned improved aluminum chlorhydrate and a zirconyl hydroxyhalide.

Preparation of Aluminum Chlorhydrate

While the aluminum chlorhydrate product of this invention can be defined as having the empirical formula $Al_2(OH)_{6-y}X_y$, where y is 0.7 to 3 and X is Cl, Br or I, it will be understood that the aluminum halohydrate of this invention has associated with it both free water and coordinated water. The empirical formula showing this water $Al_2(OH)_{6-y}X_y \cdot nH_2O$, where y and X are as previously defined and n has a numerical value of about 0.8 to about 4; preferably about 1 to about 3.5; more preferably about 2 to about 3. Approximately 85 wt. % of the water is coordinated water as contrasted with conventional Aluminum Chlorhydrates which contain about 60% coordinated water.

The process comprises reacting metallic aluminum in the form of pellets, powder, chips or bars with a hydrohalogen acid of the formula HX, where X is chlorine, bromine or iodine. Preferably the acid is HCl.

While the reaction can be carried out at a temperature of about 50° C. to about 100° C., it is preferred that the reaction is carried out at about 80° C. to about 100° C.; more preferably at about 90° C. to about 100° C.; most preferably at about 95° C. to 100° C., e.g., about 96° C. to about 98° C. The reaction is carried out in the absence of reflux conditions. Refluxing can result in reduced formation of the Band III component, and will result in the formation of pre-Band I high molecular weight polymers. However, it is within the scope of this invention to utilize a condenser to condense and return water evaporated during the process to the reaction vessel in order to maintain the proper concentration of reactants and product in the reaction mixture.

Successful practice of the invention is best achieved when the quantities of aluminum, water and acid are selected so as to result in an exotherm of at least 5° C., preferably, about 10° C. to about 20° C. The desired exotherm can be achieved by using a concentration of HCl such that the water/HCl solution formed is at least a 3 wt. % concentration of HCl in the water; preferably about 5 wt. % to about 8 wt. % % HCl. It is not necessary to premix the water and HCl in order to commence the reaction. It is preferred that they be added separately. As used in the specification and claims with reference to HCl, the concentration indicated means that concentration which a water/HCl solution would have if the quantity of water and acid utilized in the process were pre-mixed, notwithstanding the fact that pre-mixing is neither required nor preferred.

Generally, an excess of aluminum is used in carrying out the reaction process of this invention. This is so since aluminum must always be present throughout the reaction in order for the final product to be formed. However, where the aluminum is in a powdered form the reaction will go to completion using stoichiometric amounts of aluminum and HCl based on the anticipated formula of the product. For example, where the desired product is $Al_2(OH)_5Cl$ the HCl/Al ratio is determined based on that formula for aluminum chlorhydrate, and not on the stoichiometric amounts required to form aluminum chloride.

In carrying out the process of this invention the aluminum is preferably in pellet or powder form. While chemically pure aluminum can be utilized in the practice of this invention it is not preferred. The aluminum of choice contains trace amounts of iron or copper. The iron and copper catalyze the HX-Aluminum reaction, which results in substantial heat generation, thereby minimizing the amount of heating required to maintain the reaction mixture at the proper temperature.

Although the concentration of iron in the aluminum can range from about 0.02 to about 0.25 wt. % in the preparation of concentrated solutions of aluminum chlorhydrate of the prior art, in the practice of this invention the iron concentration in the aluminum must be limited to about 0.02 to about 0.1 wt. %. Reactions which use aluminum having iron impurities of greater than 0.1% result in aluminum salts having iron contents greater than the acceptable limits of the cosmetics trade. The concentration of copper in the aluminum can be about 0.005 to about 0.2 wt. %. Preferably, however, the copper content of the aluminum is about 0.005 to about 0.03 wt. %. It is of course within the scope of this invention to utilize aluminum metal containing both iron and copper.

A critical aspect of the process of this invention is the final concentration of aluminum halohydrate in the reaction mixture which must be maintained at a concentration in percent by weight in the range of about 8 to about 35%, preferably about 8 to about 25%, more preferably about 15 to about 25%, and most preferably from about 17 to about 22% by weight. Above 25 wt. % the amount of Band III in the product diminishes where the halogen is chlorine. For example at a 35% concentration the Band III component is reduced to about 20% for an aluminum chlorhydrate. While the Band III levels will be higher where the halogen is bromine, though a desirable product, Aluminum Bromhydrate is not the most preferred product.

The process can be most advantageously practiced over the entire 8 to 25 wt. % range. It is preferred, however, that the minimum concentration be at least 15 wt. %. Below 15% the solutions of product are cloudy. There appears to be a relationship between the cloudiness of the reaction solution and the development of higher molecular weight species found prior to Band II in the chromatographic distribution. When reactions are carried out in solutions having a concentration of less than 15%, the development of cloudiness can be avoided by reducing the reaction temperature and shortening the reaction time. Where the solution concentration is below 15% it is preferred that the reaction temperature is below 90° C. and that the reaction time is less than 24 hours; more preferably the reaction temperature is about 70 to about 85° C., e.g., 75° C. to about 85° C.; more specifically, 80° C.

The polymer distribution achieved by the process of this invention is one of extremely narrow polydispersity, particularly when the final batch concentration of aluminum halohydrate falls within the range of 17–22% and the metal to halogen atomic ratios are about 1.00:1 to about 2.10:1. Preferably these ratios are about 1.50:1 to about 2.00:1; more preferably about 1.90:1 to about 2.00:1. Such products derived from the process of this invention can be converted to more stable polymer forms by the hot spray drying of the solution of aluminum chlorhydrate to a dry powder utilizing conventional spray drying methods.

Spray drying is the preferred method of converting the hot aqueous basic aluminum salts of this invention to a stable powdered form. Other methods of drying such as tray drying or vacuum drying require longer periods of time for water evaporation. These drying techniques go through concentrated liquid phases, or reduced temperatures, both of which can result in a substantial loss in the Band III component and the widening of the polydispersity value of Band II, of the product of this invention. In carrying out the spray drying process the outlet drying temperature can be about 150° F. to about 275° F.; preferably about 200° F. to about 240° F.; more preferably about 210° F. to about 230° F. If the aluminum halohydrate solution is allowed to cool after completion of the reaction, and before spray drying a loss in the Band III component to a level of less than 20% results. It is preferred that the solution be filtered before spray drying.

The size exclusion chromatogram test was used to determine polymer distributions, contents and relative retention times of Bands I, II, III and IV on the samples of the compositions of this invention and samples of known compositions. This test is an analytic technique related to high performance liquid chromatogram (HPLC). In carrying out the tests a Waters Associates Model 510 pump, a U6K injector, a 401 refractive index detector, and a 730 data module were used for the HPLC instrumentation. Two micro Porasil 60 A GPC columns 3.8×30 cm (Waters Cat. No. 84190) were used in the adsorption.

The directions for carrying out the test are as follows:

In preparing the mobile phase, pipette 2 ml. conc. nitric acid in a 1 l. volumetric flask containing distilled water, dilute to mark and mix. New columns should be conditioned with this mobile phase at least three hours prior to sample testing. Turn pump on to 1.0 ml/min., flush the reference side of the refractive index cell several minutes and switch to sample side. Referring to the operator manual, zero in the R.I. detector and set the attenuation to 16X. Also set the 730 data module to the following parameter values:

| Parameter No. | Description | Value |
| --- | --- | --- |
| 2 | Chart Speed | 0.6 (cm./min.) |
| 3 | Plot Mode | 0 (Off) |
| 4 | Pen 2 | 0 (Off) |
| 5 | Pen 1 | 10 |
| 7 | Auto Zero | 0 (Off) |
| 8 | L.C. Mode | 1 (Yes) |
| 9 | Calibration | 0 (Analysis) |

-continued

| Parameter No. | Description | Value |
| --- | --- | --- |
| 20 | Auto Parameters | 0 (Off) |
| 21 | Peak Width | 7 |
| 22 | Noise Rejection | 2,000 |
| 23 | Area Rejection | 1,000 |
| 24 | Run/Stop | 6.5 (Min.) |
| 33 | Report % results | 1 (Yes) |
| 46 | Flow Rate | 1.0 (ml./min.) |
| 47 | Pressure | Column Pressure |
| 48 | Detector/Attenuation | 401/016 |
| 63 | Report Percent Only | 1001 |

The analytical procedure is as follows:

Pipette 0.2 ml. 12M hydrochloric acid into a 25 ml volumetric flask containing distilled water, dilute to mark and mix.

After the detector and columns have reached equilibrium as seen by the stability of the response on parameter 51, set parameter 51 to read 5,000–10,000 by turning the optical zero knob on the detector, being certain that operating temperatures within the room remain constant since the slightest change in the temperatures will be sensed by the R.I. detector which will create a base line drift.

Inject a 15 ml. sample of 0.1N hydrochloric acid standard and observe its retention time (the retention time in this analytical test was found to be 5.70 minutes). Set parameters 81 and 82 to retention time values off 5.40 and 6.00 minutes which will inhibit and resume integration without integrating the hydrochloric acid band itself which contains no aluminum polymers.

Dilute all basic aluminum halides to approximately a 10% active level with distilled water, filter the sample through a 0.45 m filter and inject a 3.0 ml sample for the test. The chromatogram will show which aluminum containing polymer bands are present, the retention times of each band and their calculated percentages.

Calculation:

% Band to be determined =

$$\frac{\text{(Area Percent of band to be determined)}}{\text{Total Area Percent of Al containing bands}}$$

It is known that during stages of basic aluminum halides synthesis via conventional methods of preparation, higher molecular weight polymers, pertaining to aluminum polymers of the Band I range, are developed and their percent composition against the total polymer content increases with increasing metal to chloride atomic ratios. Table I shows the percent of Band I polymers found at various reaction states of aluminum chlorhydrate preparation when prepared by the conventional method.

TABLE I

| Aluminum/Chloride Atomic Ratio | % Band I Aluminum Polymers |
| --- | --- |
| 1.32:1 | 15.9 |
| 1.82:1 | 17.0 |
| 1.93:1 | 37.2 |

In addition to the formation of Band I, it is also known that basic aluminum halides produced via conventional methods of synthesis contain lower amounts of Band III than those amounts found using the process of this invention.

The advantages of the instant invention will be more readily appreciated by reference to the following examples and the drawings. The examples are intended to be illustrative of the invention and in no way limit the scope of this invention. In the drawings FIGS. 1 to 6 illustrate chromatograms of the product showing the four (4) typical aluminum polymer bands.

EXAMPLE 1

Aluminum metal was reacted with hydrochloric acid and water, where the amount of water was stoichiometrically controlled so that the final reaction product contained a (water+hydroxyl)/aluminum molar ratio of about 9.7:1 and the active concentration was about 50%, as described below.

In a 250 ml glass reaction flask, equipped with a reflux condenser and thermometer, 30 g. of granulated aluminum was reacted with 125.8 grams of deionized water and 52 grams of 20 Baume hydrochloric acid. The batch was heated to 98° C. until nearly all the aluminum was in solution and the aluminum to chloride atomic ratio was determined by analysis to be 2.00:1. The resulting 50% solution was filtered and its polymer composition was determined by the size exclusion chromatogram test previously described. The chromatogram in FIG. 1 shows four typical aluminum containing polymer bands with relative retention times calculated with respect to the retention time of hydrochloric acid. Table II shows the retention times, relative retention times and the percent of the total aluminum polymers found in each band.

TABLE II

| Band | RI (Min.) | RRT | AL Polymer |
|---|---|---|---|
| I | 3.72 | 0.65 | 39.23 |
| II | 4.08 | 0.72 | 54.98 |
| III | 4.38 | 0.77 | 2.95 |
| IV | 4.89 | 0.86 | 2.85 |

The last unintegrated band in FIG. 1 is that of hydrochloric acid which exists as free acid to some degree in all basic aluminum chlorides. In accordance with the test procedure described in the invention this peak was eluted at 5.7 minutes and it is this retention time that is used as the basis in calculating relative retention times of all other bands. The range of relative retention times for purposes of the invention has been defined as shown in Table III.

TABLE III

| Band No. | Relative Retention Time Range |
|---|---|
| Band I | 0.62–0.70 |
| Band II | 0.71–0.75 |
| Band III | 0.76–0.82 |
| Band IV | 0.83–0.97 |

The 50% solution obtained in this example is a standard product in the industry and can be marketed as such or further processed to a basic aluminum chloride powder through common techniques such as spray drying, vacuum drying, etc.

Examples 2 to 5 illustrate the process of this invention.

EXAMPLE 2

(A) A 20% solution of aluminum chlorhydrate was prepared by reacting 2.4 kg. of granulated aluminum, 12.5 kg. of distilled $H_2O$ and 4.25 kg. 20 Baume hydrochloric acid in a 50 liter reaction flask. During the exotherm of the reaction an additional 21.47 kg. of distilled $H_2O$ was charged. The temperature of the batch was maintained at 98° C. through the oxidation reduction reaction for 72 hours. A sample was taken, filtered and tested for polymer composition using the size exclusion chromatography method previously described. The sample was also analyzed for percent aluminum, percent chloride and aluminum/chloride atomic ratio.

(B) The batch was filtered hot and immediately spray dried to a stable powder form using a No. 2 fluid nozzle on a conical bottom concurrent flow lab dryer at 320° F. inlet, 160° F., outlet and 95 PSI nozzle pressure. 7.15 kg. of an off white fine crystalline powder was obtained at the cyclone outlet which was also analyzed for percent Band III, percent polymer composition, aluminum, chloride and aluminum/chloride atomic ratio. The results for the 20% aluminum chlorhydrate and the spray dried powder are shown below.

TABLE IV

| | 20% Solution | Spray Dried Powder |
|---|---|---|
| % Aluminum | 5.00 | 24.75 |
| % Chloride | 3.38 | 16.78 |
| | Al/Cl ratio 1.94:1 | |
| % Band I | 0.0 | 0.0 |
| % Band II | 59.1 | 60.6 |
| % Band III | 39.6 | 38.1 |
| % Band IV | 1.3 | 1.3 |

EXAMPLE 3

An 8% solution of aluminum sesquichlorhydrate was prepared by reacting aluminum powder with hydrochloric acid and water as follows: 50 grams of aluminum powder and 200 grams deionized were charged to a 500 ml glass reaction flask, equipped with a thermometer and condenser. 21 grams of 31.45% hydrochloric acid was added and an immediate reaction was observed. During the exotherm of the reaction an additional 172 grams of deionized water was added and the reaction mixture was maintained at about 80° C. for 1 hour. A sample was taken, filtered and immediately tested for Band III, and polymer distribution, according to the chromatographic procedure previously described, as well as % $Al_2O_3$ and Al/Cl atomic ratio. The resulting 8% solution was shown to contain:

70.14% Band III
100.0% Polymer distribution in Bands II, III & IV
3.70% $Al_2O_3$
1.16:1 Al/Cl atomic ratio

EXAMPLE 4

39.0 grams of granulated aluminum, 238 grams of deionized water and 61.0 grams of 20 Baume hydrochloric acid were charged to a 500 ml glass reaction flask equipped with a reflux condenser and thermometer. During the exotherm of the reaction additional heat was applied and the reaction was maintained at 98° C. for 48 hours, filtered hot and analyzed. The resulting 25% aluminum sesquichlorhydrate solution contained:

25.5% Band III
100.0% Polymers in Band II, III & IV
11.40% $Al_2O_3$
1.86:1 Al/Cl atomic ratio

EXAMPLE 5

40 grams of granulated aluminum, 61.8 grams of 50% hydrobromic acid and 318 grams of deionized water were charged to a 500 ml reaction flask, equipped with a reflux condenser and thermometer. The contents were reacted at 90° C. for 50 hours, filtered and tested for percent Band III, polymer distribution, % $Al_2O_3$ and aluminum to bromide atomic ratio. The resulting 25% aluminum bromhydrate solution contained:

65.5% Band III
100.0% Polymer distribution in Bands II, III & IV
9.7% $Al_2O_3$
1.90:1 Al/Br atomic ratio In the products made by the process of this invention, Band I is not formed at any time during the reaction and Band III is formed in high percentages which results in the formation of lower polymeric forms of basic aluminum halides of narrow polydispersity. This is clearly shown in an examination of FIGS. 2 to 4.

In FIG. 2, 65.0% of the aluminum polymers in Band IV exist in a very low molecular weight low basic form which together with the free hydrochloric acid (unintegrated band) are converted into Bands II and III as the reaction proceeds to the right.

FIG. 3 shows that nearly all of Band IV and half of the free acid from FIG. 2 have further reacted and converted into Bands II and III.

FIG. 4 shows the completion of the invention process where half of Band IV, 25% of free acid and 20% of Band III which existed in the sesquichlorhydrate stage in FIG. 3 have now been converted to Band II.

EXAMPLE 6

Aluminum chlorhydrate was prepared as a 50% solution in accordance with the standard method described in U.S. Pat. No. 4,359,456. The product formed contained 12.50% aluminum and an aluminum:chloride ratio of 2.00:1. Samples of the foregoing solution were prepared by diluting with deionized water to concentrations of 10%, 15% 20% and 25%. The sample were heated for six hours at 95° C. and cooled to room temperature. A portion of the 20% solution was maintained at 95° C. for a total of 72 hours.

As a comparison a 20% basic aluminum chloride was prepared using the process of this invention at 95° C. to an Al/Cl atomic ratio of 2.00:1. The product solution was decanted from excess aluminum and maintained at 95° C. for an additional 72 hours.

All samples were tested for their polymer distribution by the size exclusion chromatography method described above. The polymer distributions are shown in FIG. 5 and are described as follows:

TABLE V

CHROMATOGRAMS-FIGS. 5A-5I

| FIGURE | DESCRIPTION |
|---|---|
| 5A | Standard 50% basic aluminum chloride solution used for tests 5B–5F. |
| 5B | 10% solution of standard basic aluminum chloride heated for 6 hrs. at 95° C. and cooled to room temperature. |
| 5C | 15% solution of standard basic aluminum chloride heated for 6 hrs. at 95° C. and cooled to room temperature. |
| 5D | 20% solution of standard basic aluminum chloride heated for 6 hrs. at 95° C. and cooled to room temperature. |
| 5E | 25% solution of standard basic aluminum chloride heated for 6 hrs. at 95° C. and cooled to room temperature. |
| 5F | 20% solution of standard basic aluminum chloride heated for 72 hrs. at 95° C. and cooled to room temperature. |
| 5G | 20% solution of basic aluminum chloride prepared by the process of this invention at 95° C., and sampled immediately for chromatogram testing. |
| 5H | 20% solution of basic aluminum chloride prepared by the method of this invention at 95° C., maintained at 95° C. for 6 hours after completion of the reaction, sampled at 95° C. and tested. |
| 5I | 20% solution of basic aluminum chloride prepared by the method of this invention at 95° C., maintained at 95° C. for 72 hours after completion of the reaction, sampled at 95° C. and tested. |

TABLE V
(Continued)
CHROMATOGRAMS-FIGS. 5A-5I

In all cases for the prior art preparation technique (FIG. 5B–5F) a Band I component exists. With respect to the product of this invention, however, (FIG. 5G–5I) no Band I component ever exists.

EXAMPLE 7

Figure 6:
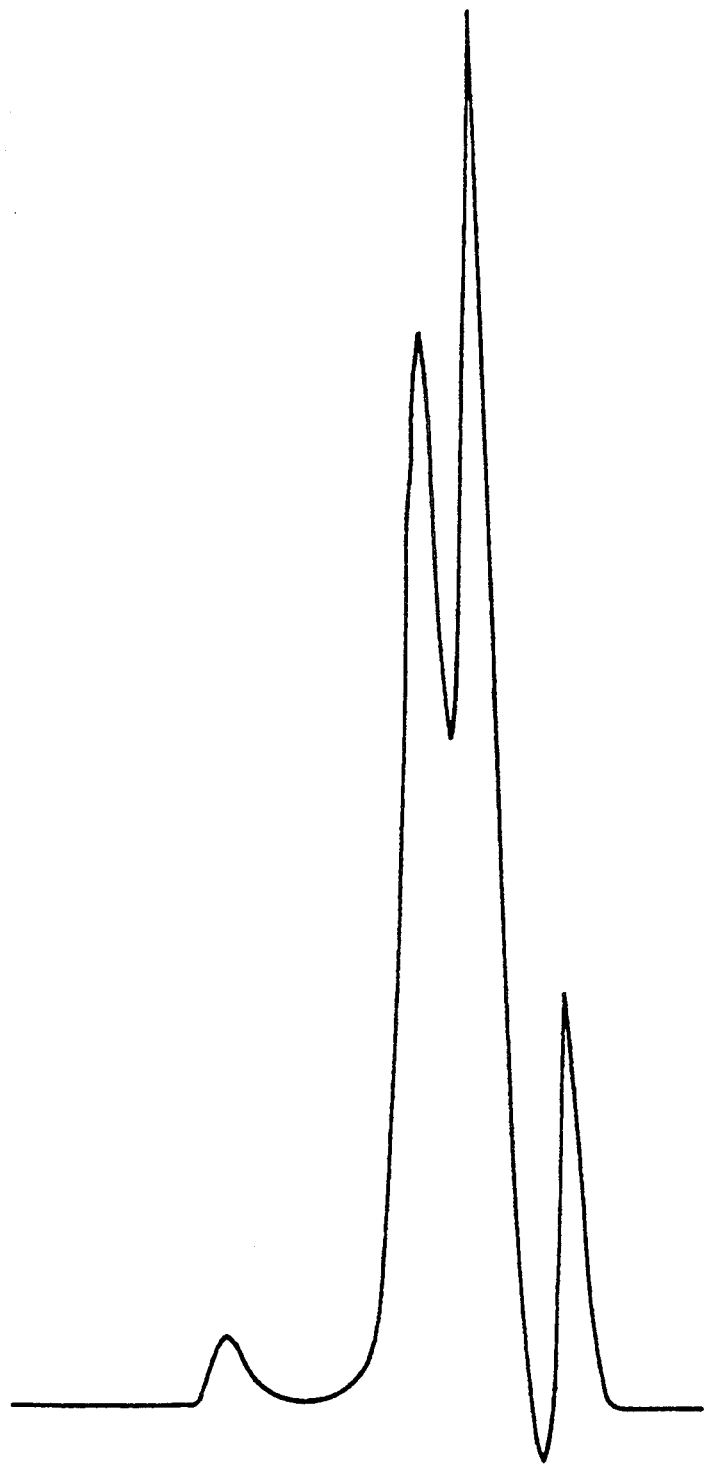
FIG. 6 is a chromatogram of 20% aqueous aluminum chlorhydrate prepared according to the process of the '456 patent by heating for 8 hours at 120° C.

Example 11 of Gosling U.S. Pat. No. 4,359,456 was repeated in the following manner. 20 grams of the standard 50% solution of aluminum chloride prepared in Example 6 was diluted with deionized water to a concentration of 10%. The solution contained 0.95M of aluminum. After heating for 8 hours at 120° C., cooled to room temperature and tested for polymer distribution by size exclusion chromatography. The sample exhibited a Band I component with 2.54% of the polymer in Band I. The chromatogram is shown in FIG. 6.

EXAMPLE 8

An aluminum chlorhydrate was prepared using the process of this invention at a concentration of 20% by heating for 72 hours at 95° C. A portion of the product was spray dried, and another portion was tray dried at 40° C. for seven days. The spray drying was carried out in the manner described in Example 2 except that the inlet temperature was 420° F. and the outlet temperature was 80° C. The chromatograms are shown in FIG. 7.

Figures 7A, 7B:
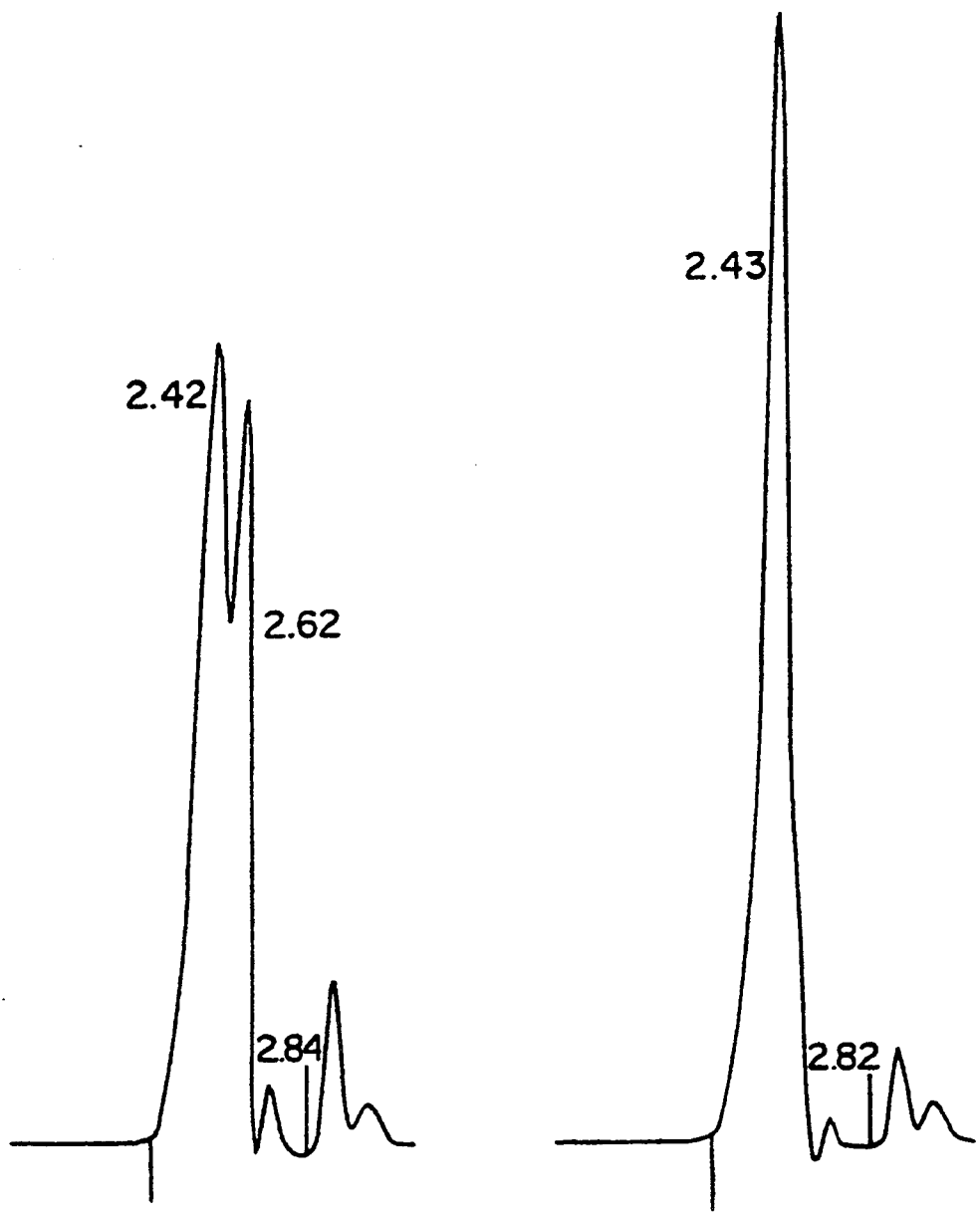
FIGS. 7A and 7B are chromatograms of the product of this invention showing the effect of spray drying and tray drying respectively.

FIG. 7A is the chromatogram for the spray dried sample which shows peaks for Bands II, III and IV. By contrast the tray dried product whose chromatogram appears in FIG. 7B shows only Bands II and IV. Therefore, it is evident that in order to maintain a Band III component of at least 25% spray drying must be utilized.

Examples 9 & 10 are outside the scope of the invention.

EXAMPLE 9

U.S. Pat. No. 3,891,745 assigned to Dynamit Nobel discloses a process for preparing aluminum chlorhydrate from HCl and Aluminum. From the disclosure and claims, and in particular the reference to pH, it is apparent that the reaction is carried out at the typical concentrated solution of the prior art. Furthermore, the example states that the end product was collected in the form of a 47% by weight solution. A scaled down in vitro experiment was conducted to reproduce the Dynamit Nobel process.

120 grams of Aluminum granules were placed in a 300 mm chromatography column fitted with a stop cock and wrapped in heating tape in the lower ⅔ section of the column. The top of the column was fitted with a water cooled condenser.

100 ml of 11% hydrochloric acid was added to the column and reaction was immediately observed. Column temperature at the lower section was maintained at about 80° C. The reaction was allowed to proceed for three hours. Before taking the first sample from the bottom valve. The contents were allowed to elute at one drop per minute from the bottom while adding another 100 ml. of 11% HCl into the top at the same rate. Two more samples were taken at 6 and 8 hours after the reaction commenced. The samples were analyzed for % Al, % Cl and Al/Cl ratio using the above described methods. The results are as follows:

TABLE VI

| Component (Chromatogram) | 3 Hr. Sample (FIG. 7A) | 6 Hr. Sample (FIG. 7B) | 8 Hr. Sample (FIG. 7C) |
| --- | --- | --- | --- |
| % Aluminum | 2.82 | 6.68 | 12.37 |
| % Chloride | 10.26 | 10.20 | 9.71 |
| Al/Cl Ratio | 0.36:1 | 0.86:1 | 1.67:1 |
| % Active Sol. | 25 | 35 | 55 |

FIG. 8 shows the size exclusion chromatography chromatograms for each sample. It is noted that the 3 hour sample (FIG. 8A) exhibited only a Band IV while the 6 and 8 hour samples, FIG. 8B & 8C respectively, exhibited Bands II & IV. None of the samples exhibited a Band III. Hence the product of the U.S. Pat. No. 3,891,745 is not the product of this invention. Therefore the process of this invention is a different process than that of the Dynamit Nobel '745 patent.

EXAMPLE 10

In comparison studies of the aluminum chlorhydrate of this invention and prior art compounds significant differences in viscosity were found. Blends of aluminum chlorhydrate were prepared with bentonite clay in formulations of the type used in cosmetic antiperspirants presently being marketed. Two blending techniques were used. Though each technique resulted in different numerical values, the trend toward higher viscosities for the blends utilizing the aluminum chlorhydrate of this invention was consistent.

DISPERSION METHOD I
Formulation:
30% Aluminum Chlorhydrate (ACH)
30% Bentone/Silicone Gel
40% Volatile Silicone The Gel and volatile silicone were homogenized together and the ACH subsequently dispersed into the mixture. The Brookfield Viscosity of the dispersion was measured after 24 hours using a No. TB spindle for the lower viscosity (below 900,000 cp) solutions and a TF spindle for the higher viscosity solutions. The viscosity comparisons are shown in Table VII. A homogenized Gel and volatile silicone mixture without ACH was used as a control.

TABLE VII
(Continued)

| BLEND ACH COMPONENT | Brookfield Viscosity (cp) | CHROMATO- GRAM FIGURE |
| --- | --- | --- |
| A. Westwood Chemical Company conventional ACH made by HCl process. | 49,000 | FIG. 9A |
| B. Activated ACH of this invention | 66,000 | FIG. 9B |
| C. Reheis Conventional ACH via AlCl$_3$ Reaction Process | 25,000 | FIG. 9C |

It will be noted that all samples containing ACH have viscosities below that of the ACH free control. Blend B which contains the ACH of this invention has a substantially higher viscosity than any of the prior art compositions. Chromatographies of the compositions are shown in FIG. 9. Blends A and C which are conventional ACH compositions have substantially identical chromatographs showing Band I, II and IV peaks but no Band III peak.

While the differences in the B and C chromatographs appear to be minor, they are significant, and there significance is evidenced by the differences in the behavior of the products in formulations as indicated by viscosity differences.

DISPERSION METHOD II

The experiment of Dispersion Method I was repeated using the same formulation except that all three component of the blend were homogenized in one step. The viscosity results are shown in TABLE VIII.

TABLE VIII

| BLEND ACH COMPONENT | Brookfield Viscosity (cp) | CHROMATO- GRAM FIGURE |
| --- | --- | --- |
| A. Westwood Chemical Company conventional ACH made by HCl process. | 2,000,000 | FIG. 9A |
| B. Activated ACH of this invention | 900,000 | FIG. 9B |
| C. Reheis Conventional ACH via AlCl$_3$ Reaction Process | 1,750,000 | FIG. 9C |
| Control | 200,000 | |

The chromatograms of these blends are of course identical to those shown in FIG. 9.

No explanation is known for the differences in viscosity response between the activated ACH of this invention and the comparison of the prior art compounds. However, not wishing to be bound by theory, it is speculated that these products react differently with the bentonite clay to give different viscosities. What is apparent is that the activated ACH of this invention is in some unexplained way different from that of other activated ACHs as evidenced by their viscosity characteristics. Hence, the process by which it is made is a different process than prior art processes.

The invention provides a reaction process for the preparation of polymeric basic aluminum halides where Band I is not formed, and at least 25% of the composition is found in Band III. A narrow distribution of polymers of low molecular weight is obtained where 100% of the aluminum containing polymers fall within chromatographic Bands II, III & IV as defined by the relative retention time ranges using the test method described within the invention. In the process of this invention no Band I component ever exists, unlike prior art processes which begin with a product containing Band I and convert the starting material to a high band III component product.

EXAMPLE 12

Figure 10:
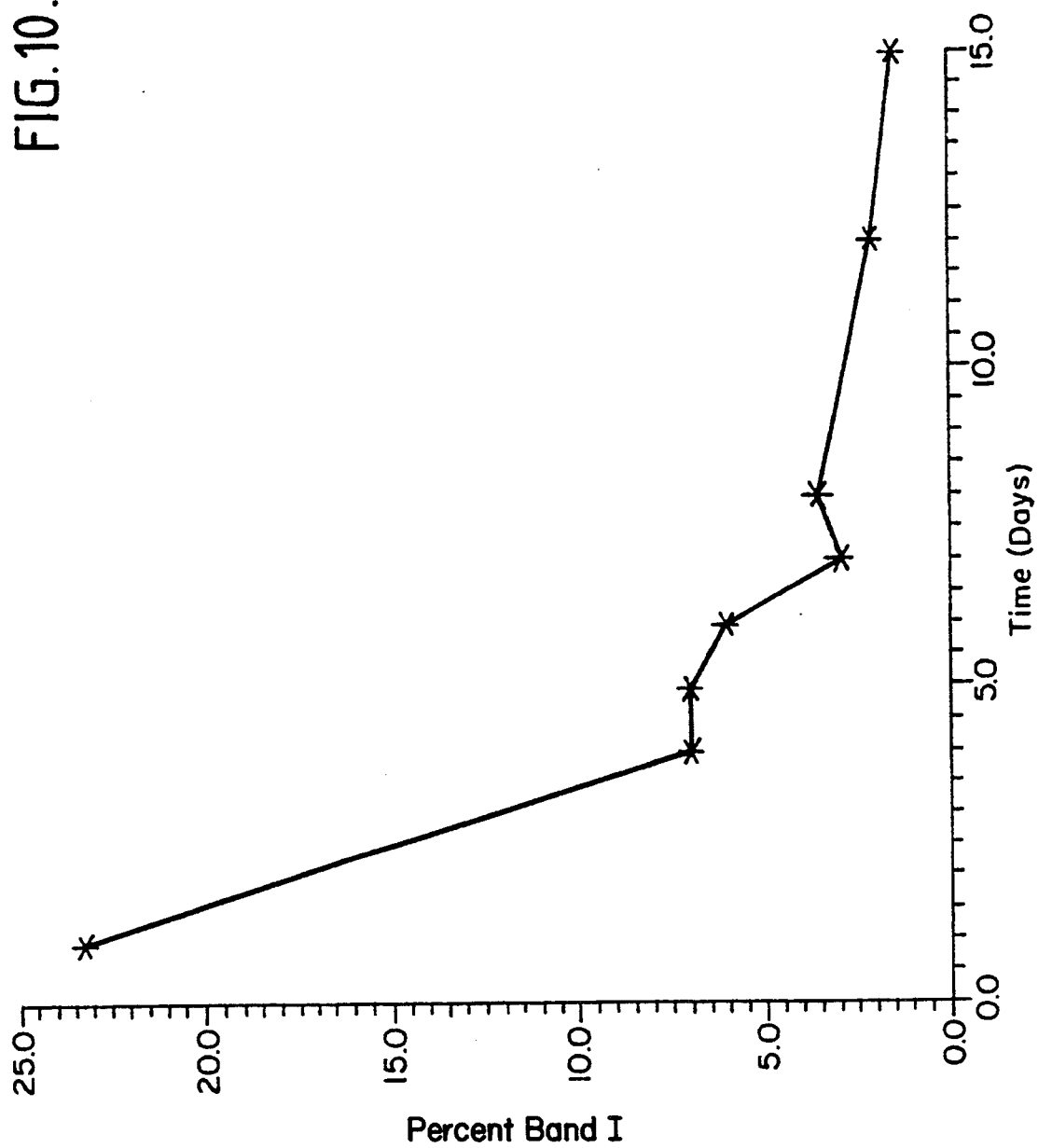

Example 16 of the Gosling U.S. Pat. No. 4,359,456 was repeated in order to determine the Band I content of the basic aluminum halide polymer produced. The results are shown in FIG. 10. It is apparent that there is an initial Band I component present in substantial amounts. With time the Band I component is reduced as Band III is produced. Nevertheless the Band I component is never extinguished even after fifteen days of heating.

What is claimed is:

1. A process for preparing a basic aluminum halide having the empirical formula:

$$Al_2(OH)_{6-y}X_y \cdot nH_2O$$

where n has a numerical value of about 0.8 to about 4, X is chlorine, bromine or iodine and y has a numerical value of about 0.7 to about 3, which comprises:
(a) reacting aluminum metal with a hydrohalogen acid having the formula HX wherein X is chlorine, bromine or iodine at a temperature of about 50° C. to about 100° C., the concentration of the product in the solution being about 8 to about 25% by weight of the solution; and
(b) recovering the basic aluminum compound from the hot solution by spray drying;
whereby the polymer distribution of the product formed as characterized by size exclusion chromatography is:
(c) 100% of the polymers are found in Bands II, III and IV, with no part of the product found in Band I; and
(d) Band III contains at least 25% of the polymer.

2. The process according to claim 1 wherein the reaction is carried out in the absence of reflux at a temperature of about 70° C. to about 100° C.

3. The process according to claim 1 wherein the reaction is carried out at a temperature of about 95° C. to about 100° C.

4. The process according to claim 1 wherein the reaction is carried out at a temperature of about 96° C. to about 98° C.

5. The process according to claim 1 wherein the acid is HCl or HBr.

6. The process according to claim 1 wherein the acid is HCl.

7. The process according to claim 1 wherein the aluminum is in the form of pellets or powder.

8. The process according to claim 1 wherein the aluminum contains copper in an amount of about 0.005 to about 0.03 wt. %.

9. The process according to claim 1 wherein the aluminum contains iron in an amount of about 0.02 to about 0.1 wt. %.

10. The process according to claim 1 wherein the concentration of product in solution is about 15 to about 25% by weight.

11. The process according to claim 1 wherein the concentration of product in the solution is about 17 to 22% by weight.

12. The process according to claim 1 wherein the aluminum is present in excess of the stoichiometric amount calculated on the acid utilized.

13. The process according to claim 1 wherein the acid concentration in the solution is at least three percent by weight.

14. The process according to claim 1 wherein the concentration of product in the solution is about 8 to about 15 wt. %, the reaction temperature is maintained at about 75° C. to about 85° C. and the reaction time is less than 24 hrs.

15. The process according to claim 1 wherein the HCl is utilized in an amount sufficient to cause an exotherm of at least 5° C.

16. The process according to claim 1 wherein the HCl is utilized in an amount sufficient to cause an exotherm of about 10° C. to about 20° C.

17. The process according to claim 1 wherein the Al/halide ratio is about 1.00:1 to about 2.10:1.

18. The process according to claim 1 wherein the Al/halide ratio is about 1.50:1 to about 2.00:1.

19. The process according to claim 1 wherein the Al/halide ratio is about 1.90:1 to about 2.00:1.

20. A basic aluminum halide product having the empirical formula $$Al_2(OH)_{6-y}X_y \cdot nH_2O$$

wherein n has a numerical value of about 0.8 to about 4, X is chlorine, bromine or iodine and y has a numerical value of about 0.7 to about 3; the product being further characterized in that 100% of the aluminum containing polymers are found in Bands II, III and IV, with no part of the product found in Band I, and Band III contains at least 25% of the polymers.

21. The basic aluminum halide according to claim 20 wherein the halide is chlorine or bromine.

22. The basic aluminum halide according to claim 20 wherein the halide is chlorine.

23. The product according to claim 20 wherein the aluminum/halide ratio is about 1.00:1 to about 2.10:1.

24. The product according to claim 20 wherein the aluminum/halide ratio is about 1.90:1 to about 2.00:1.

25. The basic aluminum halide according to claim 20 wherein said halide has the empirical formula:

$$Al_2(OH)_5 X \cdot nH_2O$$

wherein n is a numeral of about 1 to about 3.5 and X is chlorine, bromine or iodine.

26. The basic aluminum halide according to claim 25 wherein n is about 2 to about 3.

27. The basic aluminum halide according to claim 25 wherein X is chlorine.

28. The basic aluminum halide according to claim 20 wherein y has a numerical value of 1 to 2 and n is a numeral of about 1 to about 3.5.

29. The basic aluminum halide according to claim 28 wherein n is about 2 to about 3.

30. A process for preparing a basic aluminum halide having the empirical formula:

$$Al_2(OH)_{6-y}X_y \cdot nH_2O$$

where n has a numerical value of about 0.8 to about 4, X is chlorine, bromine or iodine and y has a numerical value of about 0.7 to about 3; which comprises:
(a) reacting aluminum metal containing a catalyst wherein the catalyst is about 0.02 to about 0.1 wt. % iron or about 0.005 to about 0.03 wt. % copper, with a hydrohalogen acid having the formula HX wherein X is chlorine, bromine or iodine at a temperature of about 50° C. to about 100° C., the concentration of the product in the solution being about 8 to about 25% by weight of the solution; and (b) recovering the basic aluminum compound from the hot solution by spray drying;

whereby the polymer distribution of the product formed as characterized by size exclusion chromatography is:

(c) 100% of the polymers are found in Bonds II, III and IV, with no part of the product found in Band I; and (d) Band III contains at least 25% of the polymer.

31. The process according to claim 30 wherein the Al/halide ratio is about 1.50:1 to about 2.00:1.

32. The process according to claim 30 wherein the Al/halide ratio is about 1.90:1 to about 2.00:1.

33. The process according to claim 30 wherein the halide is chloride.

34. The process according to claim 30 wherein the catalyst is iron.

35. The process according to claim 30 wherein the concentration of product in solution is about 15 to about 25 wt. %.

36. The process according to claim 30 wherein the concentration of product in solution is about 17 to about 22 wt. %.

37. The process according to claim 30 wherein the reaction temperature is about 80° C. to about 100° C.

38. The process according to claim 30 wherein the reaction temperature is about 90° C. to about 100° C.

39. The process according to claim 30 wherein the reaction temperature is about 95° C. to about 100° C.

40. The process according to claim 30 wherein the reaction temperature is about 96° C. to about 98° C.

41. The process according to claim 30 wherein the concentration of product in the solution is about 8 to about 15 wt. %, the reaction temperature is maintained at about 75° C. to about 85° C. and the reaction time is less than 24 hrs.

42. The process according to claim 30 wherein the Al/halide ratio is about 1.00:1 to about 2.10:1.

* * * * *